US010059921B2

(12) United States Patent
Williams et al.

(10) Patent No.: US 10,059,921 B2
(45) Date of Patent: Aug. 28, 2018

(54) METHODS OF MAKING SPHEROIDS INCLUDING BIOLOGICALLY-RELEVANT MATERIALS

(71) Applicant: University of Louisville Research Foundation, Inc., Louisville, KY (US)

(72) Inventors: Stuart K. Williams, Harrods Creek, KY (US); Jeremy S. Touroo, Louisville, KY (US); James B. Hoying, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 19 days.

(21) Appl. No.: 14/913,611

(22) PCT Filed: Aug. 21, 2014

(86) PCT No.: PCT/US2014/052139
§ 371 (c)(1),
(2) Date: Feb. 22, 2016

(87) PCT Pub. No.: WO2015/027086
PCT Pub. Date: Feb. 26, 2015

(65) Prior Publication Data
US 2016/0201027 A1 Jul. 14, 2016

Related U.S. Application Data
(60) Provisional application No. 61/868,246, filed on Aug. 21, 2013.

(51) Int. Cl.
*C12N 5/00* (2006.01)
*C12M 3/00* (2006.01)
*C12M 1/26* (2006.01)
*B33Y 10/00* (2015.01)
*B33Y 80/00* (2015.01)

(52) U.S. Cl.
CPC ........... *C12N 5/0012* (2013.01); *C12M 21/08* (2013.01); *C12M 33/00* (2013.01); *C12N 5/0062* (2013.01); *C12N 5/0075* (2013.01); *B33Y 10/00* (2014.12); *B33Y 80/00* (2014.12); *C12N 2513/00* (2013.01); *C12N 2533/74* (2013.01)

(58) Field of Classification Search
CPC .............. C12N 5/0075; C12N 2513/00; C12N 2533/74; C12N 5/0012; C12N 5/0062; C12M 33/00; C12M 21/08; B33Y 10/00; B33Y 80/00
See application file for complete search history.

(56) References Cited

U.S. PATENT DOCUMENTS

| 7,857,756 B2 | 12/2010 | Warren et al. |
| 2004/0096509 A1 | 5/2004 | Hutchens et al. |
| 2012/0116568 A1 | 5/2012 | Murphy et al. |
| 2012/0201890 A1 | 8/2012 | Williams et al. |

OTHER PUBLICATIONS

Kim C. et al., "Generation of core-shell microcapsules with three-dimensional focusing device for efficient formation of cell spheroid", Lab Chip, 2011, vol. 11, pp. 246-252.*
Buyukhatipoglu K. et al., "The role of printing parameters and scaffold biopolymer properties in the efficacy of a new hybrid nano-bioprinting system", Biofabrication (IOP publishing), Sep. 4, 2009, 1, 035003 (9pp) (total pp. 1-9). (Year: 2009).*
Todd, G.K., et al., Towards Neuronal Organoids: A Method for Long-Term Culturing of High-Density Hippocampal Neurons. PloS one, 2013. 8(4): p. e58996.
Hynds, R.E. and A. Giangreco, Concise review: the relevance of human stem cell-derived organoid models for epithelial translational medicine. Stem cells, 2013. 31(3): p. 417-22.
Knight, K.R., et al., Vascularized tissue-engineered chambers promote survival and function of transplanted islets and improve glycemic control. FASEB J., 2006.
Pineda, E.T., R.M. Nerem, and T. Ahsan, Differentiation Patterns of Embryonic Stem Cells in Two- versus Three-Dimensional Culture. Cells, tissues, organs, 2013.
Ng, Y.S., et al., Identification of genes involved in VEGF-mediated vascular morphogenesis using embryonic stem cell-derived cystic embryoid bodies. Lab Invest, 2004. 84(9): pp. 1209-1218.
Mason, B.N., et al., Tuning three-dimensional collagen matrix stiffness independently of collagen concentration modulates endothelial cell behavior. Acta Biomater, 2013. 9(1): pp. 4635-4644.
Vodyanik, M.A., et al., A mesoderm-derived precursor for mesenchymal stem and endothelial cells. Cell Stem Cell, 2010. 7(6): p. 718-29.
Korff, T., et al., Blood vessel maturation in a 3-dimensional spheroidal coculture model: direct contact with smooth muscle cells regulates endothelial cell quiescence and abrogates VEGF responsiveness. The FASEB journal : official publication of the Federation of American Societies for Experimental Biology, 2001. 15(2): p. 447-57.
Nunes, S.S., et al., Generation of a functional liver tissue mimic using adipose stromal vascular fraction cell-derived vasculatures. Sci Rep, 2013. 3: p. 2141.
Hiscox, A.M., et al., An islet-stabilizing implant constructed using a preformed vasculature. Tissue Eng Part A, 2008. 14(3): p. 433-40.
Tasoglu, S. and U. Demirci, Bioprinting for stem cell research. Trends Biotechnol, 2013. 31(1): p. 10-9.

(Continued)

Primary Examiner — Satyendra K Singh
(74) Attorney, Agent, or Firm — Stites & Harbison, PLLC; Terry L. Wright

(57) ABSTRACT

Methods of making a spheroid are provided whereby a suspension is first produced including one or more biologically-relevant materials dispersed within a biocompatible medium. A droplet of the suspension is then bioprinted into a salt solution by bringing the droplet into contact with a surface of the salt solution in a controlled manner to reproducibly yield a spheroid containing a desired size and a desired amount of biologically-relevant materials.

7 Claims, 7 Drawing Sheets

(56) References Cited

OTHER PUBLICATIONS

Chang, C.C., et al., Determinants of microvascular network topologies in implanted neovasculatures. Arteriosclerosis, thrombosis, and vascular biology, 2012. 32(1): p. 5-14.
Chang, C.C., et al. Direct-write bioprinting three-dimensional biohybrid systems for future regenerative therapies. J Biomed Mater Res B Appl Biomater, 2011. 98(1): p. 160-70.
Lee, W., et al., Three-dimensional bioprinting of rat embryonic neural cells. Neuroreport, 2009. 20(8): pp. 798-803.
Derby, B., Printing and prototyping of tissues and scaffolds. Science, 2012. 338(6109): p. 921-6.
Marga, F., et al., Toward engineering functional organ modules by additive manufacturing. Biofabrication, 2012. 4(2): p. 022001.
LeBlanc, A.J., et al., Adipose stromal vascular fraction cell construct sustains coronary microvascular function after acute myocardial infarction. American journal of physiology. Heart and circulatory physiology, 2012. 302(4): p. H973-82.
Nunes, S.S. et al., Vessel arterial-venous plasticity in adult neovascularization. PloS one, 2011. 6(11): p. e27332.
Nunes, S.S., et al., Implanted microvessels progress through distinct neovascularization phenotypes. Microvasc.Res., 2010. 79(1): p. 10-20.
Zuk, P.A., et al., Human adipose tissue is a source of multipotent stem cells. Molecular biology of the cell, 2002. 13 (12): p. 4279-95.
Williams, S.K., M.A. Matthews, and R.C. Wagner, Metabolic studies on the micropinocytic process in endothelial cells. Microvasc Res, 1979. 18(2): p. 175-84.
Wagner, R.C. and M.A. Matthews, The isolation and culture of capillary endothelium from epididymal fat. Microvasc Res, 1975. 10(3): p. 286-97.
Wagner, R.C., et al., Biochemical characterization and cytochemical localization of a catecholamine-sensitive adenylate cyclase in isolated capillary endothelium. Proceedings of the National Academy of Sciences of the United States of America, 1972. 69(11): p. 3175-9.
Smith, C.M. et al., Characterizing environmental factors that impact the viability of tissue-engineered constructs fabricated by a direct-write bioassembly tool. Tissue Eng, 2007. 13(2): p. 373-83.
Smith, C.M. et al., Three-dimensional bioassembly tool for generating viable tissue-engineered constructs. Tissue Eng, 2004. 10(9-10): p. 1566-76.
Pedersen, J.A., S. Lichter, and M.A. Swartz, Cells in 3D matrices under interstitial flow: effects of extracellular matrix alignment on cell shear stress and drag forces. J Biomech, 2010. 43(5): p. 900-5.
Griffith, L.G. and M.A. Swartz, Capturing complex 3D tissue physiology in vitro. Nat Rev Mol Cell Biol, 2006. 7 (3): pp. 211-224.
Akeda, K., et al., Three-dimensional alginate spheroid culture system of murine osteosarcoma. Oncology reports, 2009. 22(5): pp. 997-1003.
Sanford, G.L., et al., Three-dimensional growth of endothelial cells in the microgravity-based rotating wall vessel bioreactor. In vitro cellular & developmental biology. Animal, 2002. 38(9): pp. 493-504.
Williams, et al., Encapsulation of Adipose Stromal Vascular Fraction Cells in Alginate Hydrogel Spheroids Using a Direct-Write Three-Dimensional Printing System. BioResearch Open Access, 2013.2(6): pp. 448-454.
Foty, R. A simple hanging drop cell culture protocol for generation of 3D spheroids. J Vis Exp. May 6, 2011;(51). pii:2720. doi: 10.3791/2720.
Smith, C.M., et al., Automatic thresholding of three-dimensional microvascular structures from confocal microscopy images. J Microsc, 2007. 225(Pt 3): pp. 244-257.
Kuratnik, A., et al. Intestinal organoids as tissue surrogates for toxicological and pharmacological studies. Biochemical pharmacology, 2013.
U.S. Patent and Trademark Office, International Search Report issued in corresponding Application No. PCT/US14/52139, dated Nov. 19, 2014.

\* cited by examiner

METHODS OF MAKING SPHEROIDS INCLUDING BIOLOGICALLY-RELEVANT MATERIALS

RELATED APPLICATIONS

This application claims priority from U.S. Provisional Application Ser. No. 61/868,246, filed Aug. 21, 2014, the entire disclosure of which is incorporated herein by this reference.

TECHNICAL FIELD

The presently-disclosed subject matter relates to methods of making spheroids including biologically-relevant materials. In particular, the presently-disclosed subject matter relates to methods of making spheroids whereby a suspension containing one or more biologically-relevant materials is bioprinted and brought into contact with salt solution in a controlled manner to reproducibly yield a spheroid having a desired size and a desired amount of biologically-relevant materials.

BACKGROUND

The use of three-dimensional environments for cell culture provides a more physiological relevant system for in vitro modeling of cell behavior and for the creation of constructs for subsequent implantation. In the body, tissues are composed of multiple cell types and cells are organized in specific spatial arrangements providing orientation of cells into geometries specific to organ functions. The study of cell function in vitro, originally utilizing cells grown on tissue culture surfaces (e.g. glass and plastic) has now transitioned to three-dimensional cultures of cells that are often embedded in collagen gels. Coordinately, investigators have evaluated the ability of two- and three-dimensional cell cultures to undergo the spontaneous formation of spheroids during culture. Epithelial and endothelial organoid cultures have been established in this way [1-5]. In those procedures, embryonic stem cells were cultured as hanging drops and allowed to form embryoid bodies (EBs) [6, 7]. Spheroid culture strategies have since progressed to include endothelium, representing cells of the vasculature, a common cellular component of all complex tissues [8-10]. And recently, complex three-dimensional tissue constructs containing parenchymal cells and vascular cells have been implanted in experimental models [11, 12]. Each of those studies show that functional tissue organoids can be constructed in vitro, implanted in tissue with evidence of vascular integration between implanted and recipient circulations and with evidence that the organoids can provide restoration of tissue function.

The formation of three-dimensional cell and tissue constructs, however, has yet to be fully evaluated and realized using bioprinting technologies [13-16]. Bioprinting, the biologic equivalent of Computer Assisted Design (CAD) and subsequent Computer Assisted Manufacturing (CAM) technologies, includes several different fabrication systems including direct-write bioprinting and ink jet bioprinting [13, 17, 18]. These systems provide CAD-CAM based methods for the controlled deposition of biological materials toward the fabrication of complex biological structures. As such, any improvements to the use of bioprinting for the production of such complex biological structures would be both highly desirable and beneficial.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some implementations of the presently-disclosed subject matter, a method of making a spheroid including one or more biologically-relevant materials is provided. In some implementations, the method comprises an initial step of providing a suspension including one or more biologically-relevant materials dispersed within a biocompatible medium. That suspension is then bioprinted into a salt solution by extruding the suspension through a delivery pen and placing the resulting droplet against a surface of the salt solution. In this regard, in some implementations, the bioprinting of the droplet can be performed in a controlled manner to reproducibly yield a spheroid containing a desired size and a desired amount of biologically-relevant materials.

In some implementations of the methods, the one or more biologically-relevant materials comprises magnetic beads, one or more stromal vascular fraction cells, stem cells, one or more relevant cells, or combinations thereof. In some implementations, the biocompatible medium is a hydrogel that, in some implementations, is comprised of a material selected from the group consisting of agarose, alginate, collagen type I, a polyoxyethylene-polyoxypropylene block copolymer, silicone, polysaccharide, polyethylene glycol, and polyurethane. In some implementations, the salt solution comprises $CaCl_2$.

In other implementations of the methods for making a hydrogel spheroid described herein, the bioprinting of the spheroid can be further performed in a manner that allows for the production of a pre-vascularized spheroid. For instance, in some implementations, a method of making a pre-vascularized spheroid is providing that includes the steps of providing a first suspension that includes one or more relevant cells dispersed within a biocompatible medium, and providing a second suspension that includes one or more microvascular fragments dispersed within a biocompatible medium. A bioprinter having a first delivery pen surrounded by a second delivery pen is then provided, and the first suspension is placed in the first delivery pen, while the second suspension is placed in the second delivery pen. The first suspension and the second suspension are then extruded from the first delivery pen and the second delivery pen, respectively, in a substantially simultaneous manner such that a droplet is formed with the second suspension encapsulating the first suspension. In other words, by coextruding the first suspension and the second suspension from the first and second delivery pens at substantially the same time, a droplet is formed wherein a biocompatible medium containing one or more microvascular fragments encapsulates a core comprised of a biocompatible medium containing one or more stromal vascular fraction cells, stem cells, or one or more relevant cells. In some implementations, upon formation of the droplet, the droplet is then placed against a surface of a salt solution.

Further provided by the presently-disclosed subject matter are spheroids including one or more biologically-relevant materials that are produced by the methods described herein. Additional features and advantages of the present invention will also become evident to those of ordinary skill in the art after a study of the description, figures, and non-limiting examples in this document.

DESCRIPTION OF EXEMPLARY EMBODIMENTS

Figure 1:
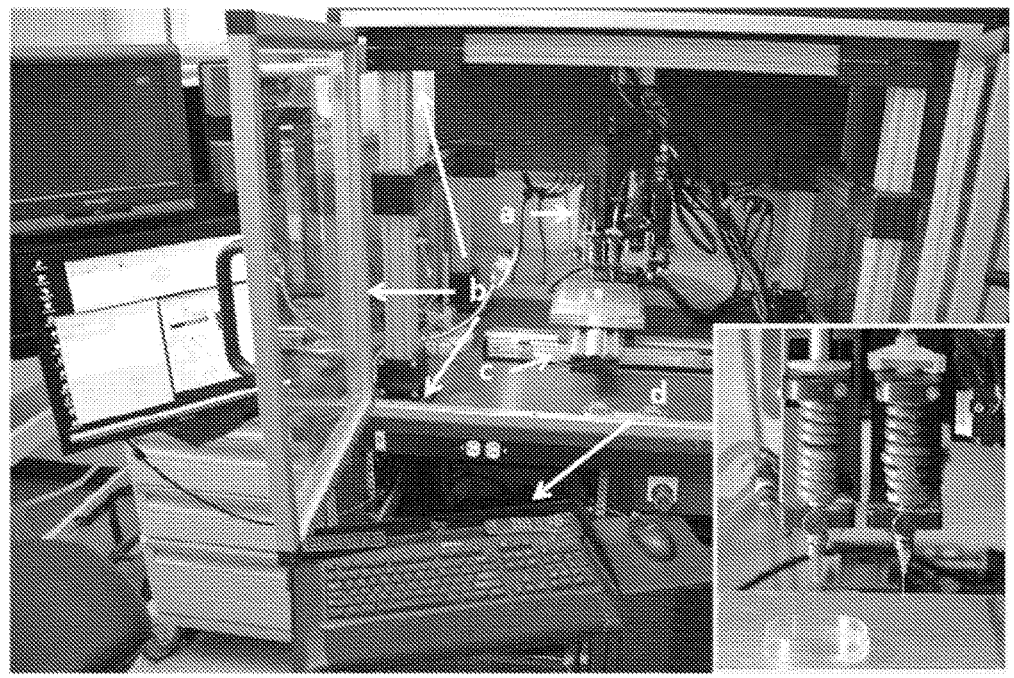
FIG. 1 includes photographs of a three-axis three-dimensional (3D) bioprinter (BioAssembly Tool (BAT)) used for the creation of adipose stromal vascular fraction (SVF) cell spheroids, where the bioprinter is composed of a pen delivery gantry with Z-axis control (a), an environmental chamber (b) housing the pen delivery gantry, a stage with X and Y axis control mounted below the pens (c), and an integrated computer system (d) for controlling the bioprinter, and where the inset photograph shows a higher magnification view of the bioprinter pen delivery gantry.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is based, at least in part, on the discovery that a direct-write bioprinting instrument can be used to form spheroids comprised of a biocompatible medium containing cells or other biologically-relevant materials. In particular, and as described in detail below, it has been determined that bioprinting systems and conditions can be configured to allow for the construction of spheroids having precisely-controlled dimensions and precise amounts of cells or other biologically-relevant materials, which then maintain their shape when cultured. In this regard, the bioprinting of the spheroids thus provides a means toward rapid fabrication of complex spheroid constructs for use in in vitro studies and for use as a controlled dose cell delivery system for regenerative medicine therapies.

In some implementations of the presently-disclosed subject matter, a method of making a spheroid is provided in which a suspension is first provided that includes one or more biologically-relevant materials dispersed within a biocompatible medium. A droplet of the suspension is then formed by bioprinting the suspension, and the resulting droplet is subsequently dispensed into a salt solution by placing the droplet against the surface of the salt solution. For instance, as one exemplary implementation of a method for making a spheroid of the presently-disclosed subject matter that makes use of direct-write printing as a form of bioprinting, in some embodiments, a BioArchitecture Tool (BAT; see, e.g., U.S. Pat. No. 7,857,756; see also Smith, et al., Tissue Eng. 2004; 10:1566-1576, both of which are incorporated herein by this reference) is utilized that makes use of a computer-controlled stage, which not only permits independent X- and Y-axis translation, but also permits z-axis movement of one or more translational print head/dispensing systems. In this regard, bioprinting parameters can first be scripted as printing instructions and then uploaded to the printing tool such that the printing tool (i.e., the BAT) can be used to produce a precise structure containing a suspension. In some embodiments, by making use of such a printing tool, the size of a droplet printed by such a system can be controlled by controlling the size of the pen used to print the droplet and by controlling the pressure with which the droplet is extruded from the pen. In some embodiments, about a 15 gauge pen to about a 25 gauge pen and a pressure of about 3 psi to about 7 psi can be used to produce a droplet, or resulting spheroid as described in detail below, having a size of about 500 microns to about 2500 microns. In some embodiments, the size of the droplets or spheroids is controlled by adjusting one or more parameters selected from the group consisting of: the viscosity of the suspension, the size of the delivery pen tip, the pressure used to extrude the suspension from the delivery pen, and the amount of time pressure is applied to the suspension in the delivery pen.

Figure 2:
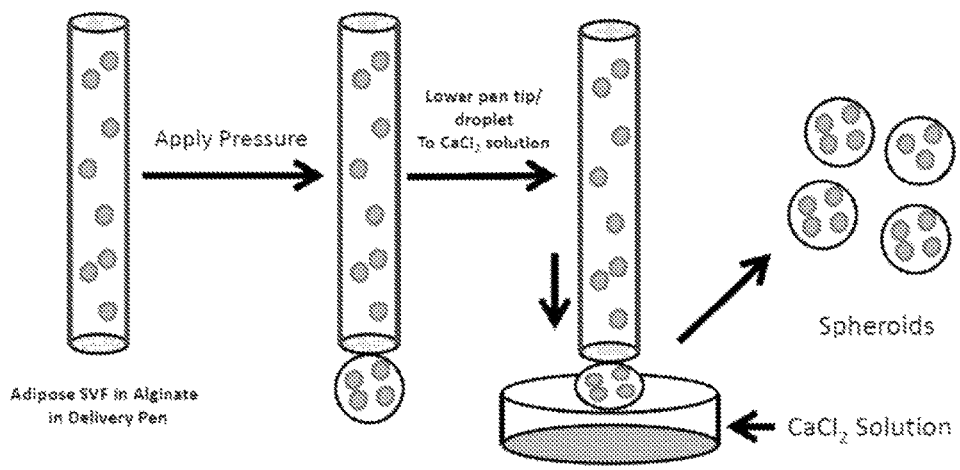
FIG. 2 is a schematic diagram showing an exemplary process for bioprinting cell- and tissue-encapsulated spheroids in accordance with the methods of the presently-disclosed subject matter where a human stromal vascular fraction cell population is mixed in 1.5% alginate and placed in a delivery pen, where extrusion of fluid is controlled by increasing the pressure in the delivery pen to a specific value causing a droplet to form, where the delivery pen is lowered toward the $CaCl_2$ solution at a rate of 5 mm/sec, and where a suspended droplet subsequently overcomes the surface tension and a spheroid forms within the $CaCl_2$ solution.

As one exemplary implementation of a method for making a spheroid including one or more biologically-relevant materials, and with reference to FIG. 2, a spheroid is produced by first placing a suspension in the form of a cell suspension (e.g., a cell suspension comprised of a human stromal vascular fraction cell population mixed in 1.5% alginate), in a delivery pen that is comprised of a hollow needle or tube-like structure. Extrusion of the biological suspension from the delivery pen is then controlled by increasing the pressure in the delivery pen to a specific value, thereby causing a droplet to form. The delivery pen is then lowered toward a salt (e.g., $CaCl_2$) solution at a predetermined rate (e.g., 5 mm/sec). Upon contacting the salt solution, the suspended droplet subsequently overcomes the surface tension and a spheroid gels and forms within the salt solution.

The term "suspension" is used herein to refer to a composition comprising biologically-relevant materials, including magnetic particles, cells, tissues, proteins, and the like that are dispersed within a biocompatible medium. A suitable biocompatible medium for use in accordance with the presently-disclosed subject matter can typically be formed from any biocompatible material that is a gel, a semi-solid, or a liquid, such as a low-viscosity liquid, at room temperature (e.g., 25° C.) and can be used as a three-dimensional substrate for cells, tissues, proteins, and other biological materials of interest. Exemplary materials that can be used to form a biocompatible medium in accordance with the presently-disclosed subject matter include, but are not limited to, polymers and hydrogels comprising collagen, fibrin, chitosan, MATRIGEL™ (BD Biosciences, San Jose, Calif.), polyethylene glycol, dextrans including chemically cross-linkable or photo-crosslinkable dextrans, and the like, as well as electrospun biological, synthetic, or biological-synthetic blends. In some embodiments, the biocompatible medium is comprised of materials that support endothelialization, see, e.g., U.S. Pat. Nos. 5,744,515 and 7,220,276, both of which are incorporated herein by reference. In some embodiments, the biocompatible medium is comprised of a hydrogel.

The term "hydrogel" is used herein to refer to two- or multi-component gels comprising a three-dimensional network of polymer chains, where water acts as the dispersion medium and fills the space between the polymer chains. Hydrogels used in accordance with the presently-disclosed subject matter are generally chosen for a particular application (e.g., a particular spheroid) based on the intended use of the structure, taking into account the printing parameters that are to be used as well as the effect the selected hydrogel will have on the behavior and activity of the biological materials (e.g., cells) incorporated into the biological suspensions that are to be placed in the structure. Exemplary hydrogels of the presently-disclosed subject matter can be comprised of polymeric materials including, but not limited to: alginate, collagen (including collagen types I and VI), elastin, keratin, fibronectin, proteoglycans, glycoproteins, polylactide, polyethylene glycol, polycaprolactone, polycolide, polydioxanone, polyacrylates, polyurethanes, polysulfones, peptide sequences, proteins and derivatives, oligopeptides, gelatin, elastin, fibrin, laminin, polymethacrylates, polyacetates, polyesters, polyamides, polycarbonates, polyanhydrides, polyamino acids carbohydrates, polysaccharides and modified polysaccharides, and derivatives and copolymers thereof as well as inorganic materials such as glass such as bioactive glass, ceramic, silica, alumina, calcite, hydroxyapatite, calcium phosphate, bone, and combinations of all of the foregoing. For additional information regarding the materials from which a hydrogel of the presently-disclosed subject matter may be comprised, see, e.g., U.S. Pat. Nos. 7,919,11, 6,991,652 and 6,969,480, each of which are incorporated herein by this reference.

With further regard to the hydrogels used to produce the spheroid, in some embodiments, the hydrogel is comprised of a material selected from the group consisting of agarose, alginate, collagen type I, a polyoxyethylene-polyoxypropylene block copolymer (e.g., Pluronic® F127 (BASF Corporation, Mount Olive, N.J.)), silicone, polysaccharide, polyethylene glycol, and polyurethane. In some embodiments, the hydrogel is comprised of alginate.

Turning now to the biologically-relevant materials included in an exemplary suspension and used in accordance with the presently-disclosed subject matter, the phrase "biologically-relevant materials" is used herein to describe materials that are capable of being included in a biocompatible medium as defined herein and subsequently interacting with and/or influencing biological systems. For example, in some implementations, the biologically-relevant materials are magnetic beads (i.e., beads that are magnetic themselves or that contain a material that responds to a magnetic field, such as iron particles) that can be combined with a hydrogel and then bioprinted along with the hydrogel to produce spheroids having a defined size that can be used in the calibration of instrumentation or for the separation and purification of cells and tissues according to methods known to those skilled in the art. As another example, in other implementations, the biologically-relevant materials include one or more cells and tissues, such that combining the cells or tissues with an appropriate biocompatible medium results in the formation of a cell or tissue suspension. In some embodiments, the biologically-relevant materials are comprised of stromal vascular fraction cells, stem cells, one or more relevant cells, or combinations thereof.

With respect to the stromal vascular fraction cells used in accordance with methods of the presently-disclosed subject matter, the stromal vascular fraction cells are those that are typically obtained by enzymatically digesting an amount of adipose tissue obtained from a subject, followed by a period of centrifugation to pellet the stromal vascular fraction of the adipose tissue. In this regard, the stromal vascular fraction contains a number of cell types, including preadipocytes, mesenchymal stem cells (MSCs), endothelial progenitor cells, T cells, B cells, mast cells, and adipose tissue macrophages, as well as small blood vessels or microvascular fragments found within the stromal vascular fraction. For further explanation and guidance regarding the disassociation of adipose tissue to produce a stromal vascular fraction, see, e.g., U.S. Pat. No. 4,820,626, the entire contents of which are incorporated herein by this reference.

With respect to the stem cells that can be utilized in accordance with the methods of the present invention, as used herein, the term "stem cells" refers broadly to traditional stem cells, progenitor cells, preprogenitor cells, precursor cells, reserve cells, and the like. Exemplary stem cells include, but are not limited to, embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including methods for isolating and culturing them, may be found in, among other places, Embryonic Stem Cells, Methods and Protocols, Turksen, ed., Humana Press, 2002; Weisman et al., Annu Rev. Cell. Dev. Biol. 17:387-403; Pittinger et al., Science, 284:143-47, 1999; Animal Cell Culture, Masters, ed., Oxford University Press, 2000; Jackson et al., PNAS 96(25): 14482-86, 1999; Zuk et al., Tissue Engineering, 7:211-228, 2001; and U.S. Pat. Nos. 5,559,022, 5,672,346 and 5,827, 735. Descriptions of stromal cells, including methods for isolating them, may be found in, among other places, Prockop, Science, 276:71-74, 1997; Theise et al., Hepatology, 31:235-40, 2000; Current Protocols in Cell Biology, Bonifacino et al., eds., John Wiley & Sons, 2000; and U.S. Pat. No. 4,963,489. One of ordinary skill in the art will understand that the stem cells and/or stromal cells that are selected for inclusion in a tissue construct are typically selected when such cells are appropriate for the intended use of a particular construct.

Finally, with respect to the relevant cells that can be utilized in accordance with the methods of the present invention, the term "relevant cells," as used herein refers to cells that are appropriate for incorporation into a spheroid of the presently-disclosed subject matter, based on the intended use of that spheroid. For example, relevant cells that are appropriate for the repair, restructuring, or repopulation of particular damaged tissue or organ will typically include cells that are commonly found in that tissue or organ. In that regard, exemplary relevant cells that can be incorporated into spheroids of the presently-disclosed subject matter include neurons, cardiomyocytes, myocytes, chondrocytes, pancreatic acinar cells, islets of Langerhans, osteocytes, hepatocytes, Kupffer cells, fibroblasts, myoblasts, satellite cells, endothelial cells, adipocytes, preadipocytes, biliary epithelial cells, and the like. These types of cells may be isolated and cultured by conventional techniques known in the art. Exemplary techniques can be found in, among other places; Freshney, Culture of Animal Cells, A Manual of Basic Techniques, 4th ed., Wiley Liss, John Wiley & Sons, 2000; Basic Cell Culture: A Practical Approach, Davis, ed., Oxford University Press, 2002; Animal Cell Culture: A Practical Approach, Masters, ed., 2000; and U.S. Pat. Nos. 5,516,681 and 5,559,022.

Regardless of the particular type of biologically-relevant materials that are combined with a biocompatible medium in accordance with the presently-disclosed subject matter, as indicated above, once the biologically-relevant materials are combined with a biocompatible medium, a droplet of the resulting suspension is then bioprinted into an appropriate salt solution. In this regard, the resulting salt solution thus allows the droplet of the suspension to gelate and form a spheroid having a more stable geometry. In some embodiments, the salt included in such a salt solution is selected from the group consisting of calcium chloride ($CaCl_2$), magnesium chloride ($MgCl_2$), or sodium chloride (NaCl). In some embodiments, the concentration of the salt included in such a salt solution is about 50 mM, about 55 mM, about 60 mM, about 65 mM, about 70 mM, about 75 mM, about 80 mM, about 85 mM, about 90 mM, about 95 mM, or about 100 mM. In some embodiments, the salt solutions can also be combined with gel forming components, such as agar, collagen, carrageenan, and/or chitosan, to create a surface of a gel/solution where the surface has a high salt content, and to thus allow for the formation of a spheroid when the spheroid is placed in contact with the salt-containing gel surface. Of course, the selection of a particular salt and salt concentration can, in some implementations, depend on the particular biocompatible medium and biologically-relevant materials utilized. However, it is appreciated that a particular salt and salt concentration can readily be selected by one skilled in the art using only routine experimentation and can be selected without departing from the spirit and scope of the subject matter described herein.

In some embodiments of the methods for making a hydrogel spheroid described herein, the bioprinting of the spheroid can be further performed in a manner that allows for the production of a pre-vascularized hydrogel spheroid. For instance, in some implementations and with reference to FIG. 12, a method of making a pre-vascularized hydrogel spheroid is provided that includes the steps of providing a first suspension that includes one or more relevant cells dispersed within a biocompatible medium, and providing a second suspension that includes one or more microvascular fragments dispersed within a biocompatible medium. A bioprinter (e.g., the B.A.T. assembly described herein above) having a first delivery pen surrounded by a second delivery pen is then provided, and the first suspension is placed in the first delivery pen, while the second suspension is placed in the second delivery pen. The first suspension and the second suspension are then extruded from the first delivery pen and the second delivery pen, respectively, in a substantially simultaneous manner, such that a droplet is formed with the second suspension encapsulating the first suspension. In other words, by coextruding the first suspension and the second suspension from the first and second delivery pens at substantially the same time, a droplet is formed wherein a biocompatible medium containing one or more microvascular fragments surrounds a core that is comprised of a biocompatible medium containing one or more stromal vascular fraction cells, stem cells, and/or one or more relevant cells. In some embodiments, upon formation of the droplet, the droplet is then placed against a surface of a salt solution to form a pre-vascularized spheroid.

The terms "microvessel fragment" or "microvascular fragment," are used interchangeably herein to refer to a segment or piece of a smaller caliber vascular tissue, such as arterioles, capillaries, and venules. Typically, a vessel or microvessel includes endothelial cells arranged in a tube surrounded by one or more layers of mural cells, such as smooth muscle cells or pericytes, and can further comprise extracellular matrix components, such as basement membrane proteins. In some embodiments, the vascular fragments are obtained from vascular tissue, such as that found in skin, skeletal muscle, cardiac muscle, the atrial appendage of the heart, lung, mesentery, or adipose tissue. In some embodiments, the vascular fragments are adipose tissue microvessel fragments that can be obtained from various adipose tissues including, but not limited to, subcutaneous fat, perirenal fat, pericardial fat, omental fat, breast fat, epididymal fat, properitoneal fat, and the like.

Still further provided, in some embodiments of the presently-disclosed subject matter, are spheroids produced by the foregoing methods. In some embodiments, a spheroid composition is provided that comprises a plurality of stromal vascular fraction cells encapsulated within a biocompatible medium, such as an alginate.

The practice of the presently disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples.

EXAMPLES

Example 1

Encapsulation of Adipose Stromal Vascular Fraction Cells in Alginate Hydrogels Using a Direct-Write Three-Dimensional Printing System Methods for Example 1

Adipose derived stromal vascular fraction (SVF) cells. Adipose SVF was derived from human fat obtained under IRB exemption, through non-ultrasonic suction-assisted liposuction of abdominal regions. The adipose SVF cell population was obtained according to established methods [24-26]. Briefly, adipose tissue was rinsed with 0.1% BSA-PBS, finely minced, and vigorously shaken in 2 mg/mL type I collagenase (Worthington Biochemical Company, Freehold, N.J., USA) for 40 min at 37° C. for optimal digestion. The SVF cells were pelleted via centrifugation, and buoyant adipocytes discarded. The pellet was then washed once more with 0.1% BSA-PBS and plated onto gelatin-coated tissue culture flasks. Adherent cells were expanded to confluence and frozen. For bioprinting, cells were thawed, plated onto gelatin-coated tissue culture flasks, grown to confluence in 5% CO2, 37° C. incubator. The cells were released from the culture surfaces and suspended in 1.5% (w/v) alginate and used immediately.

Bio Printer. The elements of the bio printer device included the computer assisted design element, the delivery system including precision controlled pen movement, and the precision liquid delivery system and the environmental chamber that maintains a sterile environment during spheroid preparation. The design and control of the bioprinter have been previously reported [15, 22, 27-29].

Suspension Cell Culture. Following bioprinting and gelation in $CaCl_2$, alginate spheroids encapsulating SVF cells were transferred to a spinner flask containing serum-supplemented culture medium using a 25 mL serological pipet. The spinner flask (125 mL MagnaFlex Microcarrier Spinner Flask (Wheaton Industries, Millville, N.J., USA) was used with a magnetic stirrer platform (MCS 104-L Biological Stirrer, Techne Inc., Burlington, N.J., USA) to provide convective mixing of the culture medium. Rotational speed of the magnetic impeller was set to 5 RPM for two days and then increased to 10 RPM for the remaining time frame. Dynamic culture was carried out in a 5% CO2, 37° C. incubator for a total of 16 days. Spheroids were removed from the spinner flask for analysis at specific time points using a 25 mL serological pipet.

Histology. In preparation for hematoxylin and eosin (H&E) staining, spheroids cultured in a spinner flask for 9 days were fixed in 1x HistoChoice diluted in Dulbecco's phosphate-buffered saline (D-PBS). The fixed spheroids were embedded in a gel block (HistoGel, Thermo Scientific, Waltham, Mass., USA), and the resulting construct was treated with 10% neutral-buffered formalin, infiltrated with paraffin, and embedded in paraffin. A microtome was used to obtain 6 µm sections, which were then stained with H&E and viewed utilizing brightfield microscopy.

SEM. Spheroids, fixed in HistoChoice/D-PBS, were prepared for scanning electron microscopy (SEM) through dehydration in a series of graded ethanol and drying using hexamethyldisilazane (HMDS). Dehydrated spheroids were exposed to two consecutive 30 minute immersions in HMDS, after which the HMDS was allowed to evaporate, resulting in dried specimens. The dried spheroids were sputter coated with gold and visualized using SEM (JSM-820 Scanning Electron Microscope, JEOL, Tokyo, Japan).

Results for Example 1

The direct-write bioprinter used in the fabrication of the adipose SVF spheroids is illustrated in FIG. 1. This instrument is referred to as the BioAssembly Tool (BAT) and is composed of a computer for creation of specific scripts to drive the delivery pens and control delivery pen conditions, a movable stage, and an environmental chamber. The inset photograph in FIG. 1 (bottom right) illustrates two delivery pens mounted on a motorized assembly that provides precision movement of the pens in the Z axis. All pen and stage movements are controlled by the integrated computer system which provided synchronized motion and dispensing for controlled delivery of cell-gel solutions.

The strategy for fabrication of the Ad-SVF spheroids is illustrated in FIG. 2. Human adipose derived stromal vascular fraction cells were suspended in 1.5% alginate and the cell/alginate suspension placed in a 3 cc delivery pen. Under computer control, the delivery pen tip was advanced above a solution of 75 mM $CaCl_2$ and a droplet of cell/alginate formed at the tip using air pressure. The pen tip was subsequently lowered into the $CaCl_2$ solution. The cycle time for droplet formation, pen lowering, spheroid formation and pen repositioning was approximately 8 seconds. This cycle time could be reduced to less than a second by reducing the dwell time at different steps.

Figure 3:
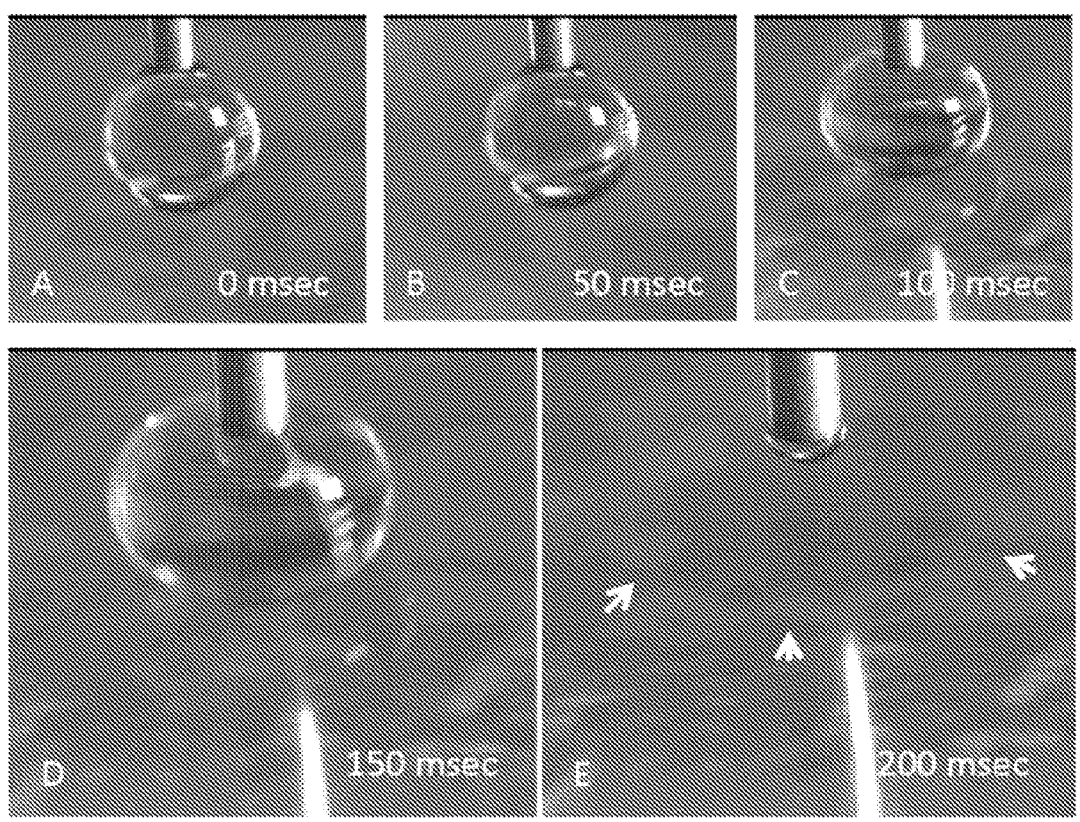
FIG. 3 includes photographs illustrating the movement of a pen tip/alginate droplet toward a $CaCl_2$ solution in accordance with the methods of the presently-disclosed subject matter, where the time sequence shown represents sequential frames (A-E) illustrating the compression of the alginate droplet against the surface of the $CaCl_2$ solution as the pen drops at a rate of 5 mm/sec, and where, in the last frame (E), the droplet has detached from the pen tip forming a spheroid and is identified with arrowheads.

A sequence of droplet formation to spheroid formation is illustrated in photomicrographs in FIG. 3. The initial droplet formation resulted in a hanging drop that remains affixed to the pen tip (18 g). The pen was then lowered toward the surface of the $CaCl_2$ solution. As seen in FIG. 3(C) and (D), as the pen advanced in the Z axis (toward the $CaCl_2$ solution), the droplet compressed/flattened against the surface. As illustrated in FIG. 3(E), the surface tension between the droplet and $CaCl_2$ solution was then overcome and a spheroid results in the $CaCl_2$ solution (edges indicated by arrows).

Figure 4:
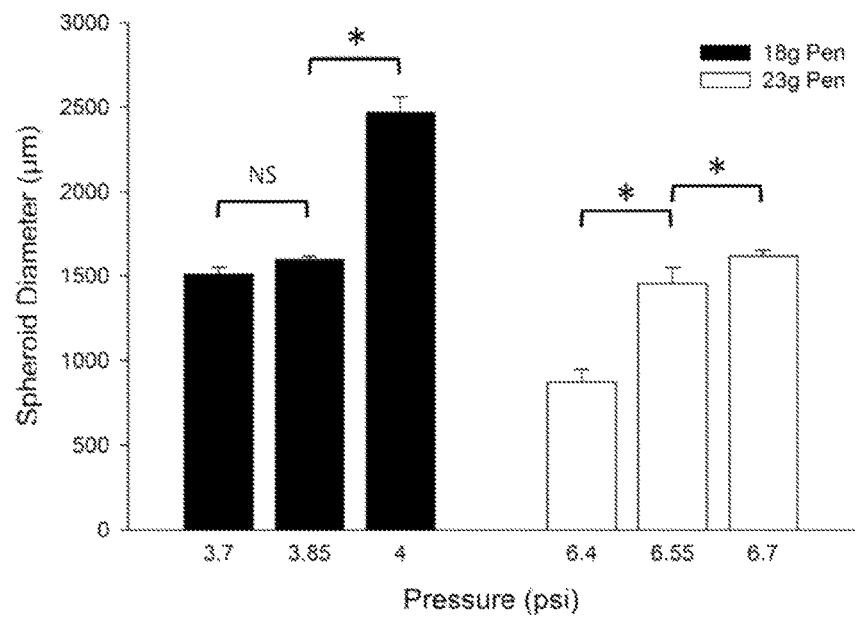
FIG. 4 is a graph showing that the size of the spheroids formed by the methods of the presently-disclosed subject matter is dependent upon both the size of the pen and the pressure used to extrude the alginate solution through the pen tip, where the data are plotted as the mean +/−standard deviation, NS=not significant, and *=significant difference ($p<0.05$) between test groups based on ANOVA statistical analysis between groups.

The ability to control the size of the formed spheroids is illustrated in FIG. 4. Two pens were used in this portion of the study (18 gauge and 23 gauge), and the pressure head during droplet formation was varied. For the 18 gauge pen, the pressure was varied between 3.7 and 4 psi resulting in a spheroid size distribution between 1,500 and 2,500 microns. For the 23 gauge pen, the pressure was varied between 6.4 and 6.7 psi resulting in a spheroid size distribution between 800 and 1,700 microns. The size distribution at each pen tip dimension and pen delivery pressure was uniform.

Figure 5:
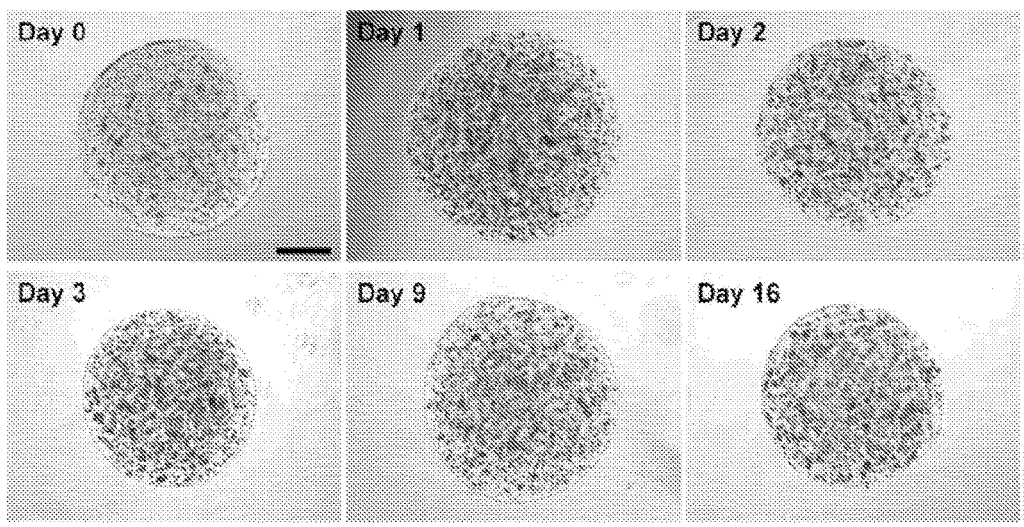
FIG. 5 includes phase contrast micrographs of adipose SVF spheroids immediately after formation (Day 0) and following culture in a spinner flask with individual culture time points identified (Bar=500 microns)
Figure 6:
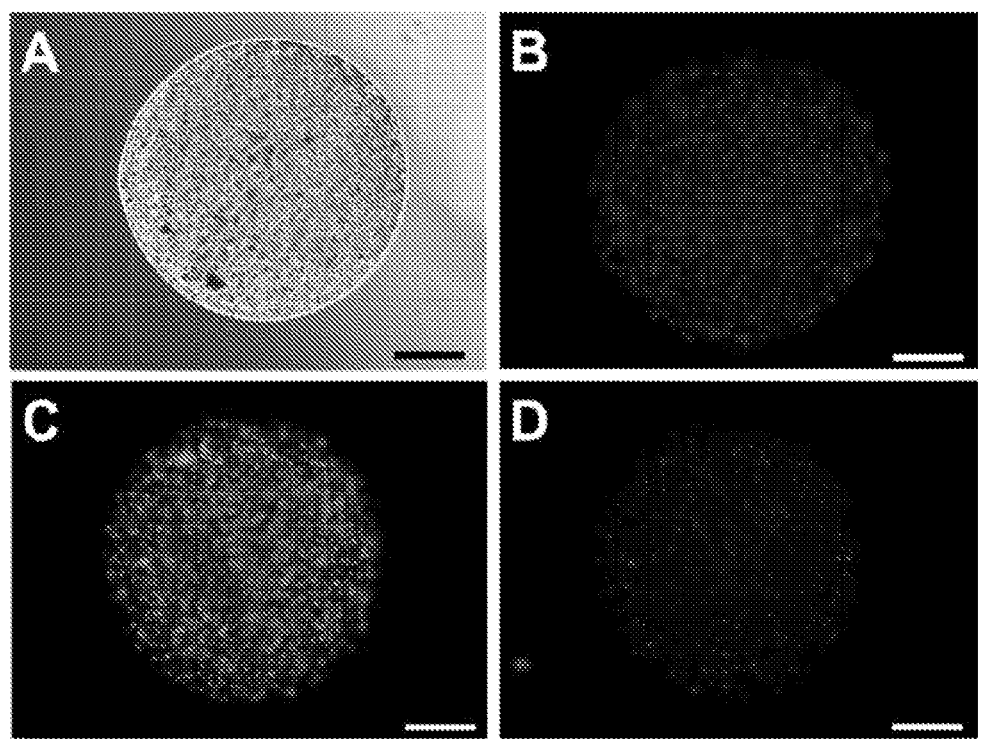
FIG. 6 includes images showing a comparison of spheroid morphology in spheroids made in accordance with the presently-disclosed subject matter and cultured for 9 days in spinner culture, where the morphology is observed by phase contrast microscopy (A), cell density and distribution using the nuclear stain bisbenzimide and visualized by epifluorescence (B), and evaluation of live (C) and dead (D) cells (Bar=500 microns)

The Ad-SVF alginate spheroids were placed in spinner suspension culture and maintained at 37° C. in a 5% CO2 environment. During a 16 day incubation period the individual spheroids remained separate with no evidence of spheroid clumping. Immediately after printing (Day 0) and also following 1, 2, 3, 9 and 16 days in suspension culture, spheroids samples were evaluated by phase contrast microscopy for spheroid integrity, encapsulated cell morphology, and cell distribution. As illustrated in FIG. 5, the spheroid size and cell distribution was maintained during the 16 days of spinner culture. FIG. 6 illustrates the distribution of cells within the spheroids after 9 days of spinner culture using phase contrast (A) and epifluorescence (B—bisbenzimide nuclear staining), and the viability of cells by evaluating live cells (C) and dead cells (D). The cell viability evaluated using this live/dead cytochemical analysis was greater than 90%.

Figure 7:
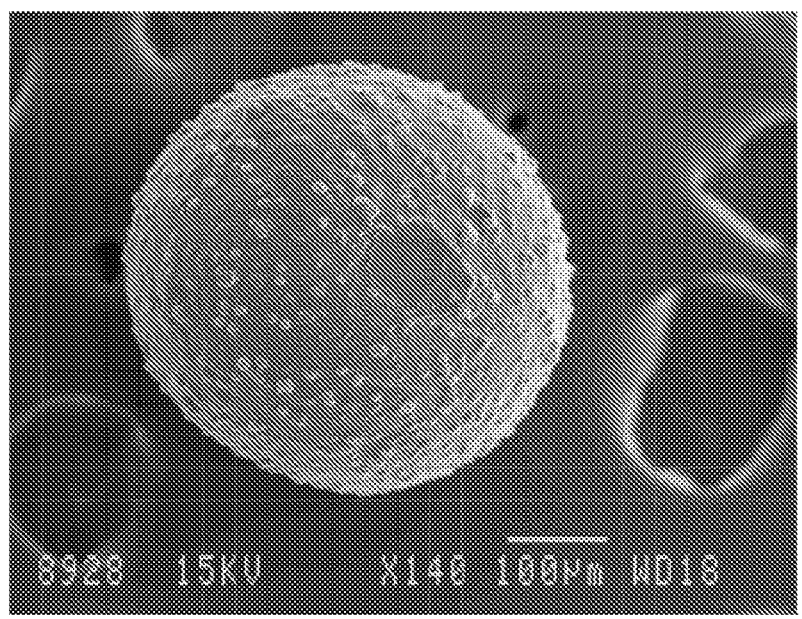
FIG. 7 is a scanning electron micrograph of an adipose SVF spheroid made in accordance with the presently-disclosed subject matter and cultured for 9 days in spinner culture (Bar=100 microns)

FIG. 7 illustrates the surface morphology of an Ad-SVF spheroid fixed immediately following printing using scanning electron microscopy. The spheroids were dried using a dehydrating solution (hexamethyldisilazane) that resulted in significant artefactual shrinkage of the spheres.

Figure 8:
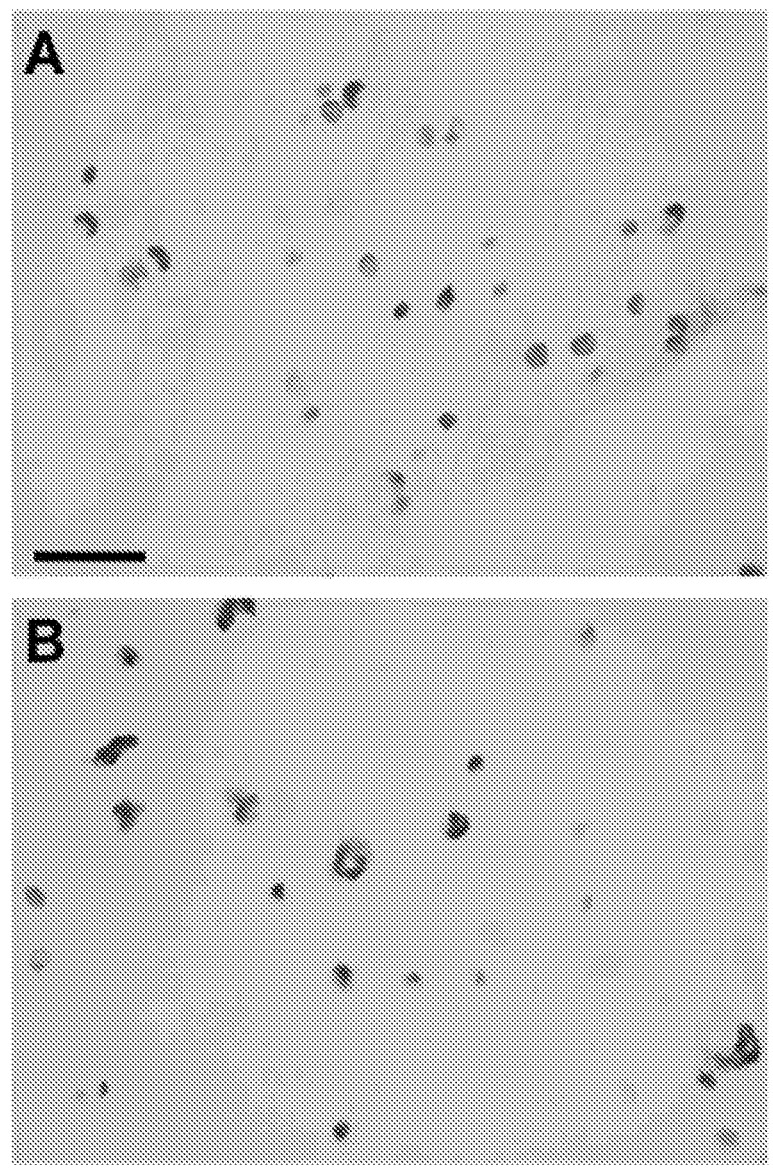
FIG. 8 includes light micrographs of hematoxylin and eosin stained sections of adipose SVF containing spheroids made in accordance with the presently-disclosed subject matter immediately after formation (A) and following 9 days in culture (B) (Bar=50 microns)

To evaluate cellular morphology within the spheroids, samples were processed for paraffin sectioning and sections stained with hemotoxylin and eosin. Representative sections (FIG. 8) illustrate the cell morphology of encapsulated cells immediately following printing (A) and after 9 days in spinner culture (B). Since the Ad-SVF cell population was composed of a number of endothelium and other vascular cells [30], the presence of tube-like structures seen in cross section in this figure was not unexpected.

Discussion of Example 1

Almost all of the cells in the body function in a three-dimensional environment. As progress is made toward recapitulation of physiological systems in tissue culture environments, the importance of establishing cells in a three-dimensional system has become apparent [31-33]. The growth of mammalian cells in 3D culture systems has included many variations including incorporation of cells in gels composed of extracellular matrix (e.g. collagen), fibrin gels, hydrogels including alginates and the self-assembly of cells into spheroids (e.g. embryoid bodies). The current study was undertaken to evaluate the use of three-dimensional bioprinting technology to create alginate spheroids that contained adipose-derived stromal vascular fraction cells. These adipose SVF containing spheroids were evaluated in suspension culture to establish the viability of encapsulated cells in prolonged culture.

Direct-write bioprinting of cells in biocompatible gel systems has been used previously to construct three-dimensional tissue mimics. Direct-write, pen-based delivery bioprinters are functionally different than ink jet based bioprinters in that the material printed can be significantly thicker or more viscous which provides opportunity for more complex structures based on the deliver pen size and pressure characteristics of the solution extrusion. In the current study a 3D bioprinter, with precise pen delivery characteristics and novel nano-dispensing pumps was used to form adipose SVF spheroids with defined dimensions.

The formation of cell-containing spheroids by placing drops of cell-containing solutions of alginate onto $CaCl_2$ has been previously reported [34], and involved manually expressing tumor cells suspended in alginate solutions through a 21 G needle where beads were formed as the alginate cell suspension penetrated a $CaCl_2$ solution. Although not directly evaluated, that formation of the alginate beads by dropping solutions onto $CaCl_2$ appeared to result in spheroids of varying size and shape. The current method, using a bioprinter to form spheroids, results in the formation of nearly perfect spheres with minimal variability between spheroids. Some advantages of bioprinting these spheroids are the ability to precisely control the volume of each alginate droplet, control the rate of alginate penetration in the $CaCl_2$ gelling solution and accelerate the process of cycling between sequences of drop formation and $CaCl_2$ penetration. The bioprinted spheroids are of uniform dimensions. As illustrated in the printing pen pressure vs. spheroid size relationship, very small changes in the pressure head driving alginate through delivery pens will result in significant changes in sphere shape. The precise control of pressure-driven drop formation results in spheroids of uniform size. These results provide evidence that bioprinting provides a method to control the quantity of cells in each spheroid and thus, control cell delivery dose wherein spheroids could be delivered directly to tissues.

The ability to culture spheroids for extended periods of time, up to 16 days, has been achieved in the foregoing studies. The spheroids could be cultured in standard cell culture dishes (data not shown) as well as in suspension cultures. The maintenance of viable cells in these suspension cultures suggested the system would be amenable to other suspension culture systems including roller bottles and microgravity simulating rotation bioreactors [35]. In the foregoing study, the adipose SVF cell population remained homogenously dispersed within the encapsulating gel. Also of interest, the diffusion of nutrients and waste products appeared to be adequate as the viable cells were observed throughout the spheroid with no evidence of a central core of dead cells.

Bioprinting of cell-containing spheroids provides a novel process to create three-dimensional cultures of mammalian cells. The spheroids are amenable to many forms of suspension culture and the use of these spheroids as a means to precisely control cell dose and cell potency offers intriguing opportunities for regenerative medicine.

Example 2

Figure 9:
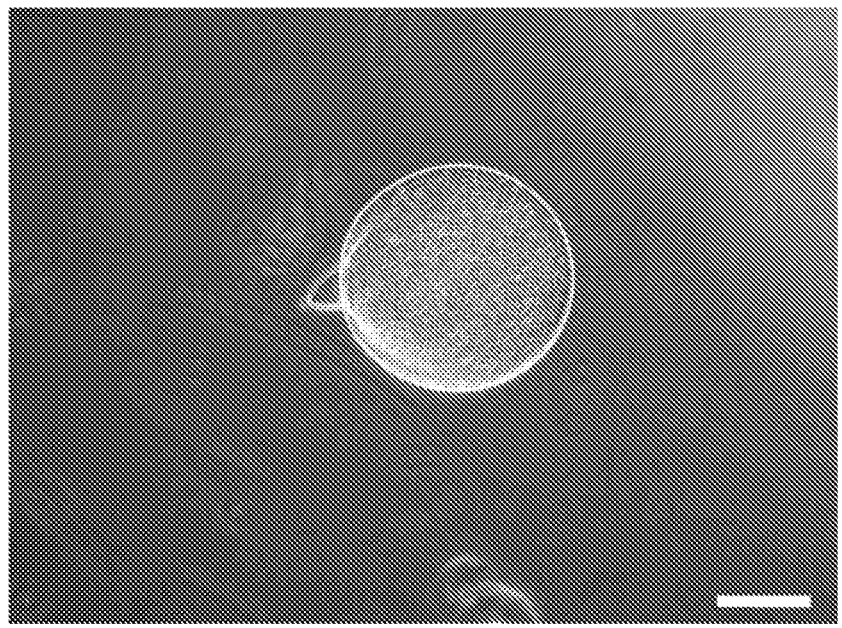
FIG. 9 is a micrograph of a magnetic bead encapsulated alginate spheroid made in accordance with the presently-disclosed subject matter (Bar=500 microns)
Figure 10:
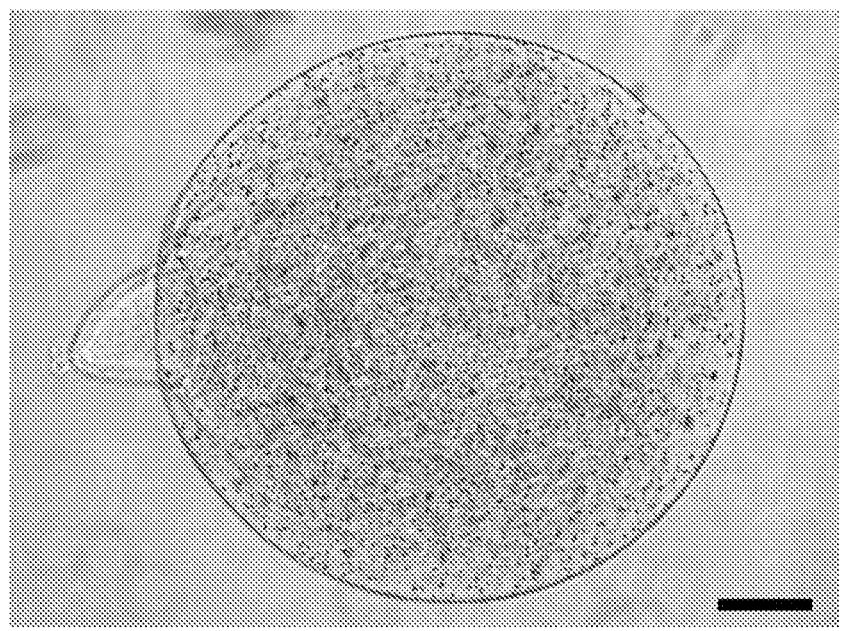
FIG. 10 is a higher magnification micrograph of a magnetic bead encapsulated alginate spheroid made in accordance with the presently-disclosed subject matter (Bar=200 microns)
Figure 11:
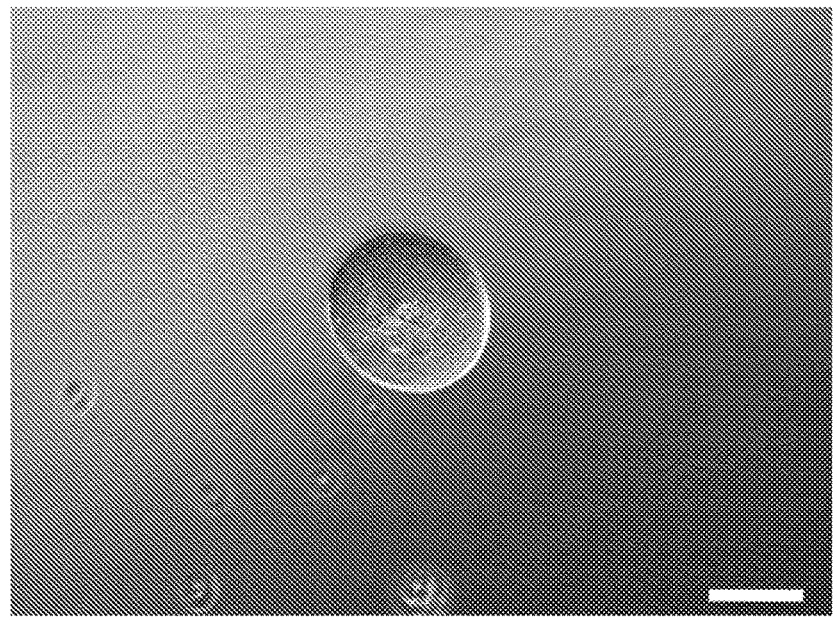
FIG. 11 is a phase-contrast photomicrograph of an alginate spheroid encapsulated made in accordance with the presently-disclosed subject matter and containing ferromagnetic particles capable of responding to a magnetic field and providing a means to move the beads to specific positions (Bar=500 microns)

Encapsulation of Magnetic Beads in Alginate Hydrogel Using a Direct-Write Three-Dimensional Printing System To evaluate the ability of the foregoing methods to controllably and reproducibly make spheroids including other biologically-relevant materials, magnetic beads (Dynabeads®, Life Technologies, Grand Island, N.Y.) were suspended in alginate and the magnetic beads/alginate suspension was placed in a 23 gauge delivery pen. Another magnetic bead (Dynabeads®) mixture was also separately suspended in alginate and the magnetic beads/alginate suspension placed in a 30 gauge delivery pen. Under computer control, the delivery pen tips were separately advanced above a solution of $CaCl_2$ and droplets formed at the tip using air pressure. The pen tips were subsequently lowered into the $CaCl_2$ solution, resulting in the production of magnetic bead-encapsulated spheroids (FIGS. 9-11), where the diameter and concentration of magnetic beads in each of the spheroids could be closely controlled and where the spheroids could then be used for magnetic particle separation instrumentation.

Example 3

Figure 12:
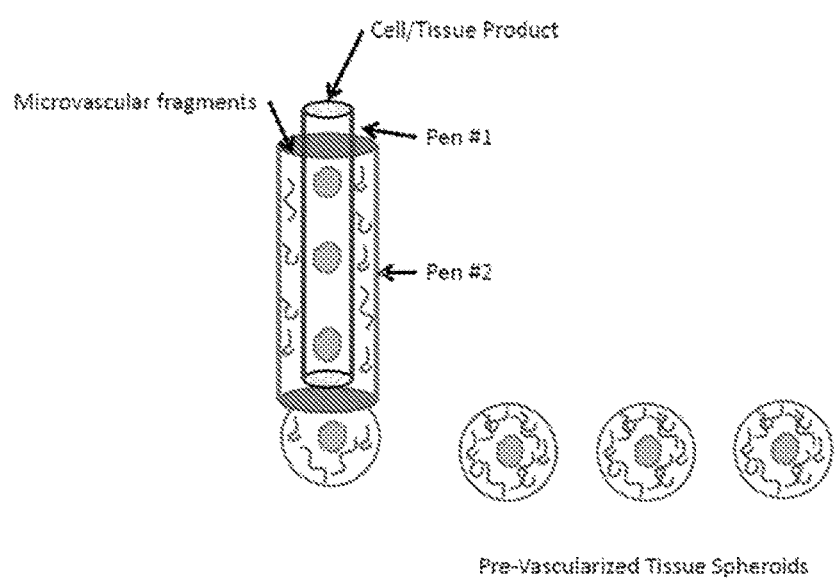
FIG. 12 is a schematic diagram showing another exemplary process for bioprinting cell- and tissue-encapsulated spheroids in accordance with the methods of the presently-disclosed subject matter that makes use of a dual-delivery pen as part of the bioprinter, where cells or tissues are mixed in alginate or another hydrogel and placed in a first delivery pen, where microvascular fragments are mixed with alginate or another hydrogel and placed in a second delivery pen surrounding the first delivery pen, and where the cell and microvascular fragment suspensions are extruded from the first and second delivery pens simultaneously so as to create a prevascularized cell or tissue encapsulated spheroid that includes an outer layer comprised of microvascular fragments and an inner core of cells or tissues.

Production of Pre-Vascularized Cell-Containing Spheroid Using a Direct-Write Three-Dimensional Printing System Including a Dual Delivery Pen To further evaluate the ability of the foregoing methods to controllably and reproducibly make spheroids, experiments were undertaken to assess the ability of the bioprinting system and methods to produce pre-vascularized spheroids. Briefly, in these experiments, the three-dimensional bioprinting system described above is again utilized. However, rather than utilizing a single delivery pen in the bioprinting system, the bioprinting system is equipped with a dual-delivery pen that includes a first delivery pen (FIG. 12, Pen #1) that is surrounded by a larger diameter pen (FIG. 12, Pen #2). A group of cells or tissues are then mixed in alginate or another hydrogel and are placed in the first delivery pen. Microvascular fragments are then mixed with alginate or another hydrogel and placed in the second delivery pen surrounding the first delivery pen. Both the cell or tissue/hydrogel suspension and the microvascular fragment/hydrogel suspension are then extruded from the first and second delivery pens simultaneously using air pressure to form a single droplets above a solution of $CaCl_2$. Upon lowering the droplet into the $CaCl_2$ solution, a prevascularized cell or tissue encapsulated spheroid is produced that includes an outer layer comprised of microvascular fragments and an inner core of cells or tissues (FIG. 12).

Throughout this document, various references are mentioned. All such references are incorporated herein by reference, including the references set forth in the following list:

REFERENCES

1. Todd, G. K., et al., Towards Neuronal Organoids: A Method for Long-Term Culturing of High-Density Hippocampal Neurons. PloS one, 2013. 8(4): p. e58996.
2. Kuratnik, A. and C. Giardina, Intestinal organoids as tissue surrogates for toxicological and pharmacological studies. Biochemical pharmacology, 2013.
3. Ewald, A. J., Isolation of mouse mammary organoids for long-term time-lapse imaging. Cold Spring Harb Protoc, 2013. 2013(2): p. 130-3.
4. Hynds, R. E. and A. Giangreco, Concise review: the relevance of human stem cell-derived organoid models for epithelial translational medicine. Stem cells, 2013. 31(3): p. 417-22.
5. Knight, K. R., et al., Vascularized tissue-engineered chambers promote survival and function of transplanted islets and improve glycemic control. FASEB J., 2006.
6. Pineda, E. T., R. M. Nerem, and T. Ahsan, Differentiation Patterns of Embryonic Stem Cells in Two- versus Three-Dimensional Culture. Cells, tissues, organs, 2013.
7. Ng, Y. S., et al., Identification of genes involved in VEGF-mediated vascular morphogenesis using embryonic stem cell-derived cystic embryoid bodies. Lab Invest, 2004. 84(9): p. 1209-1218.
8. Mason, B. N., et al., Tuning three-dimensional collagen matrix stiffness independently of collagen concentration modulates endothelial cell behavior. Acta Biomater, 2013. 9(1): p. 4635-44.
9. Vodyanik, M. A., et al., A mesoderm-derived precursor for mesenchymal stem and endothelial cells. Cell Stem Cell, 2010. 7(6): p. 718-29.
10. Korff, T., et al., Blood vessel maturation in a 3-dimensional spheroidal coculture model: direct contact with smooth muscle cells regulates endothelial cell quiescence and abrogates VEGF responsiveness. The FASEB journal: official publication of the Federation of American Societies for Experimental Biology, 2001. 15(2): p. 447-57.
11. Nunes, S. S., et al., Generation of a functional liver tissue mimic using adipose stromal vascular fraction cell-derived vasculatures. Sci Rep, 2013. 3: p. 2141.
12. Hiscox, A. M., et al., An islet-stabilizing implant constructed using a preformed vasculature. Tissue Eng Part A, 2008. 14(3): p. 433-40.
13. Tasoglu, S. and U. Demirci, Bioprinting for stem cell research. Trends Biotechnol, 2013. 31(1): p. 10-9.
14. Chang, C. C., et al., Determinants of microvascular network topologies in implanted neovasculatures. Arteriosclerosis, thrombosis, and vascular biology, 2012. 32(1): p. 5-14.
15. Chang, C. C., et al., Direct-write bioprinting three-dimensional biohybrid systems for future regenerative therapies. J Biomed Mater Res B Appl Biomater, 2011. 98(1): p. 160-70.
16. Lee, W., et al., Three-dimensional bioprinting of rat embryonic neural cells. Neuroreport, 2009. 20(8): p. 798-803.
17. Derby, B., Printing and prototyping of tissues and scaffolds. Science, 2012. 338(6109): p. 921-6.
18. Marga, F., et al., Toward engineering functional organ modules by additive manufacturing. Biofabrication, 2012. 4(2): p. 022001.
19. Leblanc, A. J., et al., Adipose stromal vascular fraction cell construct sustains coronary microvascular function after acute myocardial infarction. American journal of physiology. Heart and circulatory physiology, 2012. 302(4): p. H973-82.
20. Nunes, S. S., et al., Vessel arterial-venous plasticity in adult neovascularization. PloS one, 2011. 6(11): p. e27332.
21. Nunes, S. S., et al., Implanted microvessels progress through distinct neovascularization phenotypes. Microvasc.Res., 2010. 79(1): p. 10-20.
22. Chang, C. C., et al. In vitro patterned microvessels lose alignment in vivo. in Microcirculatory Society Meeting. 2010.
23. Zuk, P. A., et al., Human adipose tissue is a source of multipotent stem cells. Molecular biology of the cell, 2002. 13(12): p. 4279-95.
24. Williams, S. K., M. A. Matthews, and R. C. Wagner, Metabolic studies on the micropinocytic process in endothelial cells. Microvasc Res, 1979. 18(2): p. 175-84.
25. Wagner, R. C. and M. A. Matthews, The isolation and culture of capillary endothelium from epididymal fat. Microvasc Res, 1975. 10(3): p. 286-97.
26. Wagner, R. C., et al., Biochemical characterization and cytochemical localization of a catecholamine-sensitive adenylate cyclase in isolated capillary endothelium. Proceedings of the National Academy of Sciences of the United States of America, 1972. 69(11): p. 3175-9.
27. Smith, C. M., et al., Characterizing environmental factors that impact the viability of tissue-engineered constructs fabricated by a direct-write bioassembly tool. Tissue Eng, 2007. 13(2): p. 373-83.
28. Smith, C. M., et al., Automatic thresholding of three-dimensional microvascular structures from confocal microscopy images. J Microsc, 2007. 225(Pt 3): p. 244-57.
29. Smith, C. M., et al., Three-dimensional bioassembly tool for generating viable tissue-engineered constructs. Tissue Eng, 2004. 10(9-10): p. 1566-76.
30. Williams, S. K., et al., Liposuction-derived human fat used for vascular graft sodding contains endothelial cells and not mesothelial cells as the major cell type. Journal of Vascular Surgery, 1994. 19(5): p. 916-923.
31. Kellar, R. S., et al., Three-dimensional fibroblast cultures stimulate improved ventricular performance in chronically ischemic canine hearts. Tissue engineering. Part A, 2011. 17(17-18): p. 2177-86.
32. Pedersen, J. A., S. Lichter, and M. A. Swartz, Cells in 3D matrices under interstitial flow: effects of extracellular matrix alignment on cell shear stress and drag forces. J Biomech, 2010. 43(5): p. 900-5.
33. Griffith, L. G. and M. A. Swartz, Capturing complex 3D tissue physiology in vitro. Nat Rev Mol Cell Biol, 2006. 7(3): p. 211-24.
34. Akeda, K., et al., Three-dimensional alginate spheroid culture system of murine osteosarcoma. Oncology reports, 2009. 22(5): p. 997-1003.
35. Sanford, G. L., et al., Three-dimensional growth of endothelial cells in the microgravity-based rotating wall vessel bioreactor. In vitro cellular & developmental biology. Animal, 2002. 38(9): p. 493-504.
36. Williams, et al., Encapsulation of Adipose Stromal Vascular Fraction Cells in Alginate Hydrogel Spheroids Using a Direct-Write Three-Dimensional Printing System. BioResearch Open Access, 2013. 2(6): p. 448-454.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of making a pre-vascularized spheroid, comprising:
providing a first suspension including one or more relevant cells dispersed within a biocompatible medium;
providing a second suspension including one or more microvascular fragments dispersed within a biocompatible medium;
providing a bioprinter having a first delivery pen surrounded by a second delivery pen;
placing the first suspension in the first delivery pen and the second suspension in the second delivery pen; and
extruding the first suspension from the first delivery pen and the second suspension from the second delivery pen in a substantially simultaneous manner such that a droplet is formed with the second suspension encapsulating the first suspension.

2. The method of claim 1, wherein the one or more relevant cells comprises stromal vascular fraction cells.

3. The method of claim 1, wherein the biocompatible medium is a hydrogel.

4. The method of claim 3, wherein the hydrogel is comprised of a material selected from the group consisting of agarose, alginate, collagen type I, a polyoxyethylene-polyoxypropylene block copolymer, silicone, polysaccharide, polyethylene glycol, and polyurethane.

5. The method of claim 4, wherein the hydrogel is comprised of alginate.

6. The method of claim 1, further comprising a step of placing the droplet against a surface of a salt solution.

7. The method of claim 6, wherein the salt solution comprises $CaCl_2$.

* * * * *